United States Patent
Zeika et al.

(10) Patent No.: US 10,431,747 B2
(45) Date of Patent: Oct. 1, 2019

(54) QUINOID COMPOUNDS AND THEIR USE IN SEMICONDUCTING MATRIX MATERIALS, ELECTRONIC AND OPTOELECTRONIC STRUCTURAL ELEMENTS

(71) Applicant: Novaled GmbH, Dresden (DE)

(72) Inventors: Olaf Zeika, Thiessen (DE); Ina Steudtner, Dresden (DE); Andrea Lux, Dresden (DE); Steffen Willmann, Dresden (DE)

(73) Assignee: Novaled GmbH, Dresden (DE)

( * ) Notice: Subject to any disclaimer, the term of this patent is extended or adjusted under 35 U.S.C. 154(b) by 304 days.

(21) Appl. No.: 15/271,836

(22) Filed: Sep. 21, 2016

(65) Prior Publication Data

US 2017/0012203 A1    Jan. 12, 2017

Related U.S. Application Data

(62) Division of application No. 12/667,440, filed as application No. PCT/DE2008/001080 on Jul. 2, 2008, now Pat. No. 9,490,432.

(30) Foreign Application Priority Data

Jul. 4, 2007 (DE) ........................ 10 2007 031 220

(51) Int. Cl.
| | | |
|---|---|---|
| *H01L 51/00* | (2006.01) | |
| *C09K 11/02* | (2006.01) | |
| *C09K 11/06* | (2006.01) | |
| *C07C 22/08* | (2006.01) | |
| *C07C 255/51* | (2006.01) | |
| *H01L 51/50* | (2006.01) | |
| *H01L 51/52* | (2006.01) | |

(52) U.S. Cl.
CPC ............ *H01L 51/005* (2013.01); *C07C 22/08* (2013.01); *C07C 255/51* (2013.01); *C09K 11/025* (2013.01); *C09K 11/06* (2013.01); *H01L 51/002* (2013.01); *H01L 51/0051* (2013.01); *C09K 2211/1007* (2013.01); *C09K 2211/1011* (2013.01); *C09K 2211/1029* (2013.01); *C09K 2211/1044* (2013.01); *C09K 2211/1074* (2013.01); *C09K 2211/1092* (2013.01); *H01L 51/5012* (2013.01); *H01L 51/5072* (2013.01); *H01L 51/5088* (2013.01); *H01L 51/5092* (2013.01); *H01L 51/5096* (2013.01); *H01L 51/5203* (2013.01); *Y02E 10/549* (2013.01)

(58) Field of Classification Search
None
See application file for complete search history.

(56) References Cited

U.S. PATENT DOCUMENTS

| | | | |
|---|---|---|---|
| 2,566,208 | A | 8/1951 | Jenkins |
| 3,083,242 | A | 3/1963 | Ramsden |
| 3,226,450 | A | 12/1965 | Blazejak et al. |
| 3,558,671 | A | 1/1971 | Martin |
| 3,563,751 | A | 2/1971 | Cohen |
| 4,003,943 | A | 1/1977 | Fukunaga |
| 4,066,569 | A | 1/1978 | Lim |
| 4,133,821 | A | 1/1979 | West et al. |
| 4,618,453 | A | 10/1986 | Kim |
| 4,960,916 | A | 10/1990 | Pazik et al. |
| 5,093,698 | A | 3/1992 | Egusa |
| 5,110,835 | A | 5/1992 | Walter et al. |
| 5,247,226 | A | 9/1993 | Sato et al. |
| 5,281,730 | A | 1/1994 | Zambounis et al. |
| 5,292,881 | A | 3/1994 | Berneth et al. |
| 5,393,614 | A | 2/1995 | Nakada |
| 5,556,524 | A | 9/1996 | Albers |
| 5,811,833 | A | 9/1998 | Thompson |
| 5,840,217 | A | 11/1998 | Lupo et al. |
| 5,922,396 | A | 7/1999 | Thompson et al. |
| 6,013,384 | A | 1/2000 | Kido et al. |
| 6,013,982 | A | 1/2000 | Thompson et al. |
| 6,103,459 | A | 8/2000 | Diel et al. |
| 6,207,835 | B1 | 3/2001 | Reiffenrath et al. |
| 6,350,534 | B1 | 2/2002 | Boerner et al. |
| 6,423,429 | B2 | 7/2002 | Kido et al. |
| 6,524,728 | B1 | 2/2003 | Kijima et al. |
| 6,700,058 | B2 | 3/2004 | Nelles et al. |
| 6,747,287 | B1 | 6/2004 | Toguchi et al. |
| 6,824,890 | B2 | 11/2004 | Bazan et al. |
| 6,908,783 | B1 | 7/2005 | Kuehl et al. |
| 6,972,334 | B1 | 12/2005 | Shibanuma et al. |
| 7,081,550 | B2 | 7/2006 | Hosokawa et al. |
| 7,345,300 | B2 | 3/2008 | Qin |

(Continued)

FOREIGN PATENT DOCUMENTS

| | | |
|---|---|---|
| CA | 2549309 | 9/2005 |
| CH | 354065 | 5/1961 |

(Continued)

OTHER PUBLICATIONS

Akiba, Kin-Ya et al., "Direct Synthesis of 2,2-diaryl-3-methyl-2,3-dihydrobenzothiazoles from 3-methyl-2,3-dihydrobenzothiazole-2-thione and some mechanistic aspects," Bulletin of the Chemical Society of Japan, vol. 52(1), pp. 156-159, (1979).

Akutagawa, T. et al. "Multi Electron and Proton-Transfer System Based on 2,2'-biimidazole derivatives," Science and Technology of Syn. Metals, 1994, 346.

Alonso, R. A. et al. "Photostimulated Reaction of Diphenylarsenide and Diphenylstibide Ions with Haloaromatic Compounds by the Srn1 Mechanism. Electron Transfer vs. Bond Breaking of the Radical Anion Intermediate," J. Org. Chem. (1982) 47(1) pp. 77-80.

(Continued)

*Primary Examiner* — Jay Yang
(74) *Attorney, Agent, or Firm* — Eversheds Sutherland (US) LLP

(57) ABSTRACT

The invention relates to quinoid compounds and their use in semiconductive matrix materials, electronic and optoelectronic structural elements.

14 Claims, No Drawings

(56) References Cited

U.S. PATENT DOCUMENTS

| | | | |
|---|---|---|---|
| 2003/0064248 | A1 | 4/2003 | Wolk et al. |
| 2003/0165715 | A1 | 9/2003 | Yoon et al. |
| 2003/0234397 | A1 | 12/2003 | Schmid et al. |
| 2004/0068115 | A1 | 4/2004 | Lecloux et al. |
| 2004/0076853 | A1 | 4/2004 | Jarikov |
| 2005/0040390 | A1 | 2/2005 | Pfeiffer et al. |
| 2005/0061232 | A1 | 3/2005 | Werner et al. |
| 2005/0072971 | A1 | 4/2005 | Marrocco et al. |
| 2005/0086251 | A1 | 4/2005 | Hatscher et al. |
| 2005/0110009 | A1 | 5/2005 | Blochwitz-Nimoth et al. |
| 2005/0121667 | A1 | 6/2005 | Kuehl et al. |
| 2006/0049397 | A1 | 3/2006 | Pfeiffer et al. |
| 2006/0251922 | A1 | 11/2006 | Liao et al. |
| 2007/0026257 | A1 | 2/2007 | Begley et al. |
| 2007/0058426 | A1 | 3/2007 | Sokolik et al. |
| 2007/0090371 | A1 | 4/2007 | Drechsel et al. |
| 2007/0116984 | A1 | 5/2007 | Park et al. |
| 2007/0145355 | A1 | 6/2007 | Werner et al. |
| 2007/0252140 | A1 | 11/2007 | Limmert et al. |
| 2008/0103315 | A1 | 5/2008 | Egawa et al. |
| 2008/0122345 | A1 | 5/2008 | Sakata et al. |
| 2008/0145708 | A1 | 6/2008 | Heil et al. |
| 2008/0265216 | A1 | 10/2008 | Hartmann et al. |
| 2009/0001327 | A1 | 1/2009 | Werner et al. |

FOREIGN PATENT DOCUMENTS

| | | |
|---|---|---|
| CH | 354066 | 5/1961 |
| DE | 19836408 | 2/2000 |
| DE | 10261662 | 7/2004 |
| EP | 1000998 | 5/2000 |
| EP | 1596445 | 11/2005 |
| JP | 61254582 | 11/1986 |
| JP | 63172274 | 7/1988 |
| JP | 63172275 | 7/1988 |
| JP | 04338760 | 11/1992 |
| JP | 7168377 | 7/1995 |
| JP | 2004010703 | 1/2004 |
| JP | 2004335557 | 11/2004 |
| WO | WO 2003/088271 | 10/2003 |
| WO | WO 2003/104237 | 12/2003 |
| WO | WO 2006/067800 | 6/2006 |
| WO | WO 2008/022633 | 2/2008 |

OTHER PUBLICATIONS

Auch et al. "Eine neue Synthese und die Kristallstrukturanalyse von., Krokonat-Blau . . . ," Chem. Ber. 120, 1691-1696 (1987), extract, pp. 1691-1693, 6 total pages.
Bach, U. et al. "Solid-state dye-sensitized mesoporous TiO$_2$ solar cells with high photon-to-electron conversion efficiencies," Nature, vol. 395, Oct. 8, 1998, pp. 583-585.
Bamgboye, T.T. et a. "Lewis acidity of Ph2SbX3, wherein X=Cl or Br. Crystal structures of Ph2SbC13*H20 and Ph2SbBr3*MeCN," J. of Organometallic Chem. vol. 362, Feb. 28, 1989, pp. 77-85.
Bard, A. J., Faulkner, R.J., Electrochemical Methods: Fundamentals and Applications, Wiley, 2$^{nd}$ Ed., 2000 (Chapter 6).
Barton, D.H.R. et al. "Comparative Arylation Reactions with Pentaphenylbismuth and with Triphenylbismuth Carbonate," J. Chem. Soc. Chem. Commun. (1980) 17, pp. 827-829.
Baumgartel, H. et al., "Polarographische Untersuchungen zur Konformation von 1.2.3.4.5-pentaarylimidazoliumkationen," Ber. Bunsenges (1972) 76/2, 94-100.
Baumgartel, H. et al.,"Uber eine neue Synthese von tetraaryl-imidazolen und pentaaryl-imidazolium-salzen," Chem. Ber. (1968), 101, 3504.
Bhattacharya, S.N. et al. "Preparation & Characterization of Some Triarylarsenic & Triarylantimony Mixed Halides & Related Compounds," Indian J. Chem. 16A (1978) pp. 778-781.

Blinka et al. "Octacyanotetramethylenecyclobutane Dianioin and its Anion-Radical," Tetrahedron Lett. (1983). vol. 24, No. 1567-1568.
Blochwitz, J., et al., "Low voltage organic light emitting diodes featuring doped phthalocyanine as hole transport material," Applied Physics Letters, vol. 73, No. 6, Aug. 10, 1998, pp. 729-731.
Bonati, F. et al. "Reactions of C-imidazolyllithium derivatives with Broup Ib compounds: tris[micro-(1-alkylimidazolato-N3, C2)]tri-gold (I) and -silver (I)," J. Organomet. Chem. 1989, 375, pp. 147-160.
Brucsis, L. et al. "Substituionasreaktionen an 1,4-dihalogen-2,3,5,6-tetracyan-benzolen," Chem. Ber. 109(1976) pp. 2469-2474.
Cherkashin M. I. et al. "Studies on 2,4,5-triarylimidazoles," Izv. Akad. Nauk Sssr, Seriya Khim. 1982, 2, pp. 376-377.
Chonan et al. "The synthesis of difluoro and dimethyl derivatives of 2,6-bis(dicyanomethylene)-2,6-dihydro-4H-cyclopenta[2,1-b:3,4-b']-dithiophen-4-one (CPDT-TCNQ) and the Conducting Properties of the Metallic Salts Based on the Dimethy Derivative," The Chemical Society of Japan (2004) pp. 1487-1497.
Curini, M. et al., "Ytterbium Triflate Promoted Synthesis of Benzimidazole Derivatives," Synlett, No. 10, pp. 1832-1834, 2004.
Dedik, S.G. et al. "Tetrahalotetraazafulvalenes-new strong electron acceptors," Chemistry of Heterocyclic Compounds (A Translation of Khimiyageterotsiklicheskikh Soedinenii), Plenum Press Co., New York, U.S., vol. 10, Jan. 1, 1989, p. 1421.
Deluca, Mark et al., "The p-toluenesulfonic acid promoted synthesis of 2-substituted benzoxazoles and benzimidazoles from diacylated precursors," Tetrahedron, vol. 53, No. 2, pp. 457-464, 1997.
Endo, Jun et al., "Organic Electroluminescent Devices with a vacuum-deposited Lewis Acid doped hole injecting layer," Japan Society of Applied Physics, vol. 41, 2002, pp. L358-L360, Part 2, No. 3B, Mar. 15, 2002.
Fatiadi et al. "Electrochemical Oxidation of Several Oxocarbon Salts in N,N-dimethylformamide," J. Electroanalytical Chem. (1982) vol. 135, pp. 193-209.
Fatiadi, "Psuedooxocarbons, Synthesis of 1,2,3-tris(dicyanomethylene)croconate Salts; A New Bond-Delocalized Dianion, Croconate Blue," J. Org. Chem. 1980, 45, 1338-1339.
Fatiadi, "Synthesis of 1,3-(dicyanomethylene)croconate Salts. New Bond-Delocalized Dianion, Croconate Violet," Journal of the American Chemical Society, Apr. 12, 1978, pp. 2586-2587.
Fausett, B.W. et al. "Palladium-catalyzed coupling of thiol esters with aryl and primary and secondary alkyl organiindium reagents," J. Org. Chem. (2005) 70(12) pp. 4851-4853.
Fenghong Li et al., "Leuco Crystal Violet as a dopant for n-doping of organic thin films of fullerene C60," J. Phys. Chem. B 2004, 108, pp. 17076-17088.
Fild, Manfred et al. "Group VA pentafluorophenyl compounds. 14. Pentafluorophenyl-substituted phosphoranes," Zeitschrift Fuer Anorganische and Allgemeine Chemie, 439, pp. 145-152 (1978).
Fukunaga, T. et al. "Negatively substituted trimethylenecyclopropane dianions," J. Am. Chem. Soc., 1976, pp. 610-613.
Gan, F. "Optical nonlinearity of hybrid and nanocomposite materials prepared by the Sol-Gel method," J. of Sol-Gel Science and Technology, 13, 559-563 (1998).
Ganzorig, C. et al., "p-Typed Semiconducts of Aromatic Diamines Doped with SbC15," Chemistry Letters 2000, pp. 1032-1033.
Gibbons, M.N. et al. "Multiply Bridged Diantimony Compounds," Phosphorus, Sulfur, & Silicon 93/94 (1994).
Giovanella, et al. "Electroluminescence from two fluorinated organic emitters embedded in polyvinyl carbazole," Applied Physics Letters, vol. 87, pp. 171910-1-171910-3.
Glemser, O. et al. "Synthese von Tris-pentafluorphenylarsin, -stibin und -phosphin sowie von Trimethyl-pentafluor-phenylsilan," Angew. Chemie (1964) 76, 953.
Gogoi, P. et al. "An efficient and one-pot synthesis of imidazolines and benzimidazoles via anaerobic oxidation of carbon-nitrogen bonds in water," Tetrahedron Lett. 2006, 47, pp. 79-82.
Gregg, B.A. et al., "On the superlinear increase in conductivity with dopant concentration in excitonic semiconductors," Applied Physics Letters, vol. 84, No. 10, Mar. 8, 2004, pp. 1707-1709.
Grimmett, M. R., "Imidazole and benzimidazole synthesis," Tables of Contents, pp. 1-10, Academic Press, Harcourt Brace & Company, Publishers, London, San Diego, NY, Boston et al., 1997.
Gufeng, He et al., "High-efficiency and low-voltage p-i-n electrophosphorescent organic light-emitting diodes with double-emission layers," Applied Physics Letters, vol. 85, No. 17, 2004-10-25, pp. 3911-3913.

(56) References Cited

OTHER PUBLICATIONS

Haddon, R.C. et al., "Conducting films of C60 and C70 by alkali-metal doping," Nature, vol. 350, Mar. 28, 1991, pp. 320-322.
Harada, Kentaro et al., "Realization of organic pn-homojunction using a novel n-type doping technique, Proceedings of SPIE—The international Society for Optical Engineering; Organic Optoelectronics and Photonics 2004," vol. 5464, Sep. 2004, pp. 1-9.
Harris, G. S. et al."The Reaction of Trispentafluorophenylstibine with Halogens and Interhalogens," J. Fluorine Chem. 37 (1987) pp. 247-252.
Heinze, J. et al., "Polarographic studies of the conformation of 1,2,3,4,5-pentaarylimidazolium cations," The Institute for Physical Chemistry at the University of Freiburg, pp. 1-22, 1972.
Hill, J. "Oxidative Dimerization of Benzimidazole," J. Org. Chem. 1963, 28, pp. 1931-1932.
Hopf et al. "Uber einen neuen Kohlenwasserstoff C18H24 . . . ," Helvetica Chimica Acta, vol. XLIV, Issue II (1961), No. 46, extract from p. 380-386.
Hopf et al., "Preparation and Properties, Reactions, and Applications of Radialenes," Angewandte Chemie, vol. 31, No. 8, Aug. 1992, pp. 931-954.
Iyoda, et al. "Novel synthesis of hexaaryl[3]radialenes via dibromo[3]dendralenes," Tetrahedron Letters 41 (2000), 6 pgs.
Japp, F. et al. "Constitution of Glycosine," J. Chem. Soc. Trans. 1887, 51, pp. 552-557.
Jefferson, Alan M. and Suschitzky, H., "New Route to Nucleophilically Substituted o-phenylenediamines," J.C.S. Chem. Comm. pp. 189-190, 1997.
Jensen, W.B.; The Generalized Lewis Acid Based Concepts, John Wiley & Sons, New York, 1980, pp. 113-195.
Ji, L. et al. "Mono-, di- and tetra-nuclear ruthenium (II) complexes containing 2,2'-p-phenylenebis(imidazo[4,5-f]phenanthroline): synthesis, characterization and third-order non-linear optical properties," J. Chem. Soc., Dalton Trans. 2001, pp. 1920-1926.
Katz, H.E. et al., "Pyridyl Dicyanoquinodimethane Acceptors for Electroactive Solids," J. Org. Chem. 56 (1991) pp. 5318-5324.
Kaufhold, Von Jurgen et al., "Uber das Leitfahigkeitsverhalten verschiedener Phthalocyanine im Vakuum und unter dem Einfluss von gasen," Ber. Bunsen. Phys. Chem. 69, pp. 168-179.
Kikuchi, A et al. "A new family of pi-conjugated delocalized biradicals: electronic structures of 1,4-bis(2,5-diphenylimidazol-4-ylidene)cyclohexa-2,5-diene," J. Phys. Chem. B., 2005, 109, pp. 19448-19453.
Kikuchi, A. et al. "Definitive Evidence for the Contribution of Biradical Character in a Closed-Shell Molecule, Derivative of 1,4-Bis-(4,5-diphenylimidazol-2-ylidene)cyclohexa-2,5-diene," J. Am. Chem. Soc. 2004, 126, pp. 6526-6527.
Kimura, M. et al. "Preparation of 4-(4,5-diphenyl-1H-imidazol-2-yl)benzaldehyde and Its Practical Synthetic Use in the Synthesis of Unsymmetrically Substituted Imidazoles," Ite Letters on Batteries, New Technologies and Medicine, 2002, 3, pp. 30-34.
Klopman, G. "Chemical Reactivity and the Concept of Charge-and Frontier-controlled reactions," Journal of the American Chemical Society., vol. 90, No. 2, Jan. 17, 1968, pp. 223-234.
Koster, et al. "Synthesis and reactions of a tetraquinocyclobutane," Dept. of Chemistry, Univ. of Wisconsin, J. Org. Chem., vol. 40, No. 16, 1975, pp. 2300-2304.
Kozaki, M. et al. "Preparation, Properties, and Reduction of Heteroaromatic Quinoids with 1,4-diazacyclopentadien-2-ylidene Terminals," Org. Lett. 2005, 7, pp. 115-118.
Krebs, F.C. et al. "Superradiant properties of 4,4'-bis(1H-phenanthro[9,10-d] ycloalka-2-yl)biphenyl and how a laser dye with exceptional stability can be obtained in only one synthetic step," Tetrahedron Lett. 2001, 42, pp. 6753-6757.
Kulkarni, A.P. et al., "Electron transport materials for organic light-emitting diodes," Chem. Mater. 2004, 16, pp. 4556-4573.
Lane, E.S. "A Modified Benziminazole Synthesis," J. Chem. Soc. 1953, pp. 2238-2240.
Lehmstaedt, K. et al. "Halogen-2,2'-diimidazole and ihre Umsetzungen mit Aminen zu Farbstoffen," Ber. Dt. Chem. Ges. B, 1943, pp. 879-891.
Leyden, R. et al. "Thermally Induced Degradation of 2,3,5,6-tetrachloroterephthalylidenebis(o-aminoaniline)," J. Org. Chem. 1983, 48, pp. 727-731.
Li, J. Y. et al. "Enhancement of green electroluminescence from 2,5-di-p-anisyl-isobenzofuran by double-layer doping strategy," Preparation and Characterization, vol. 446, No. 1, pp. 111-116.
Ludvik, J. and Pragst, F. et al., "Electrochemical generation of triplet states," Journal of Electroanalytical Chemistry, No. 180, pp. 141-156, (1984).
Ludvik, J. and Volke, J. "Evidence for a radical intermediate in the anodic oxidation of reduced nicotinamide adenine dinucleotides obtained by electrogenerated chemiluminescence," Analytica Chimica Acta, 209 (1988) 69-78.
Maennig, B. et al., "Organic p-i-n solar cells," App. Phys. 2004, A 79, pp. 1-14.
Matschke, M. et al. "Bis-4h-imidazoles-tetraazafulvalenes-2,2'-biimidazoles: three variations of one redox system," Tetrahedron, vol. 62, No. 36, 4 Sep. 2006, pp. 8586-8590.
Mayer, U. et al. "Uber 2,3,6,7-tetraphenyl-1,4,5,8-tetraazafulvalen," Tetrahedron Lett. 1966, 42, pp. 5221-5223.
Mayer, U. et al. "Uber Biradikale, Chinone and Semichinone der Imidazolyl-Reihe," Angew. Chem. 1966, 78, p. 303.
Minoura, M. et al. "Hexaaryltellurium, the First Neutral Compounds Comprising Hexarylated Elements," Angew. Chem. Int. Edit. 35 (22) pp. 2660-2662 (1996).
Miyasato, M. et al. "Syntheses and Reactions of Hexavalent Organitellurium Compounds Bearing Five or Six Tellurium-Carbon Bonds," Chem.—A European J. 10(10) pp. 2590-2600 (2004).
Muramatsu, T. et al, "Visible Light Sensitive Cyclomer and Its Tautomeric Dispiro Compound Formed from Bispyridiny Diradical," J. Am. Chem. Soc. 2005, 127, 4572-3.
Muramatsu, T. et al., "Photosensitive Cyclomer Formation of 1,1'-(1,2-ethanediyl)bis(pyridinyl) diradical and its derivativese," J. Am. Chem. Soc. 1989, 111, 5782-7.
Muramatsu, T. et al., "Preparation and Properties of a novel heterocyclic dispiro compound, 3, 10-diaza-N,N-dimethyldispiro[5.0.5.3]pentadeca-1,4,8,11-tetraene," Chemistry Letters, pp. 151-152, (1996).
Nelsen, Stephen, F.; "Heterocyclic Radical Anions. II. Naphthalic and 1,4,5,8-Naphthalenetetracarboxylic Acid Derivatives," Journal of the American Chemical Society, 89:23, Nov. 8, 1967, pp. 5925-5931.
Oeter, D. et al., "Doping and Stability of Ultrapure alpha-oligothiophene Thin Films," Synthetic Metals, 61, 1993, pp. 147-150.
Okada, K. et al. "Detection of a diradical intermediate in the cis-trans isomerization of 5,5'-bis(4,5-diphenyl-2H-imidazol-2-ylidene)-5,5'-dihydro-delta 2,2'-bithiophene," Tetrahedron Lett. 2006, 47, pp. 5375-5378.
Okada, K. et al. "Novel Dimers of 2,2'-(m-Phenylene)bis(4,5-diphenyl-1-imidazolyl) Diradical," Chem. Lett. 1998, pp. 891-892.
Otero, A. et a. "Pentachlorophenyl-arsenic, -antimony and -bismuth compounds," J. of Organometallic Chemistry, vol. 171, No. 3, Jan. 1, 1979, pp. 333-336.
Otero, A. et al. "Pentafluorophenylantimony compounds," J. Organometallic Chem. 154 (1978) pp. 13-19.
Ouchi, A. et al. "13C-nuclear magnetic resonance of some triaryl- and tri-alkylantimony and -bismuth derivatives," J. of Inorganic and Nuclear Chemistry, vol. 37, Issue 11, Nov. 1975, pp. 2347-2349.
Ouchi, A. et al. "The syntheses and properties of some alkylthioacetato and arylthioacetato derivatives of triphenylantimony(V) and -bismus (V)," J. of Inorganic and Nuclear Chemistry, vol. 37, Issue 12, Dec. 1975, pp. 2559-2561.
Park, S. B. et al. "Highly Efficient, Recyclable Pd(II) Catalysts with Bisimidazole Ligands for the Heck Reaction in Ionic Liquids," Organic Lett. 2003, 5, pp. 3209-3212.
Parthasarathy, G. et al., "Lithium doping of semiconducting organic charge transport materials," J. Appl. Phys., vol. 89, No. 9, May 1, 2001, pp. 4986-4992.

(56) References Cited

OTHER PUBLICATIONS

Petzhold, C. "Beitrage zur Synthese funktioneller 1,4,5,8-tetraazafulvalene," Dissertation; Friedrich-Schiller-Universitat Jena; 2006.
Pfeiffer, M, et al., "Doped Organic semiconductors: physics and application in light emitting diodes," Organic Electronics, Elsevier, Amsterdam, NL, vol. 4, No. 2/3, Sep. 2003 (Sep. 2003), pp. 89-103, XP001177135, ISSN: 1556-1199.
Quast, H. and Schmitt, E.; "Note Regarding the Quaternization of Heterocycles," Institute of Organic Chemistry at the University of Wurzburg, Chem. Ber. 101, pp. 4012-4014, (1968).
Rake, A. T. et al. "Pentafluorophenyl and phenyl-phosphinidene ions and their group V analogues," Oms. Organic Mass Spectrometry, vol. 3 Jan. 1, 1970, pp. 237-238.
Rasmussen, P.G. et al. "Complexes of the New Ligand Tetracyanobiimidazole," J. Am. Chem. Soc. 1982, 104, pp. 6155-6156.
Rezende, M. C. et al. "An Alternative Preparation of Bisbenzimidazoles," Syn. Comm. 2001, 31, pp. 607-613.
Rezende, M. et al. "Puzzling Formation of Bisimidazole Derivatives from Hexachloroacetone and Diamines," Tetrahedron Lett. 1996, 37, 5265-5268.
Sakaino, Y. "Structures and Chromotropic Properties of 1,4-bis(4,5-diphenylimidazol-2-yl)benzene Derivatives," J. Org. Chem. 1979, 44, pp. 1241-1244.
Sato, S. et al. "Isolation and Molecular Structure of the Organopersulfuranes [12-S-6(C6)]," J. Am. Chem. Soc. 128(21) pp. 6778-6779 (2006).
Schmidt, "Reaktionen von Quadratsaure and Quadratsaure-Derivaten," Synthesis, Dec. 1980, extract pp. 966, 24 total pages.
Schneiders, P. et al. "Notiz zur Darstellung von 4,4',5,5'-tetrasubstituierten Di-2-imidazolyl-derivaten. Ausgangsprodukte zur Darstellung von 1,4,5,8-tetraazafulvalenen," Chem. Ber. 1973, 106, pp. 2415-2417.
Schwarz, W. M. et al., "Formation of Stable Free Radicals on Electroreduction of N-alkylpyridium salts," J. Am. Chem. Soc., 33 3164 (1961).
Seitz, G., Nachr. Chem. Tech. Lab 28 (1980), No. 11, extract pp. 804-807, total pp. 6: "Pseudooxokohlenstoffe."
Sekine, T. et al. "Dimerizations of pi-Rich N-heteroaromatic compounds and xanthine derivatives," Chem. Pharm. Bull. 1989, 37, pp. 1987-1989.
Sharma, G.D. et al., "Influence of Iodine on the Electrical and Photoelectrical Properties of Zinc Phthalocyanine Think Film Devices," Materials Science and Engineering, B41, 1996, pp. 222-227.
Singhal, K. et al. "One the Lewis acidity of tris(pentafluorophenyl)antimony (V) dichloride towards neutral monodentate O, N and S donor ligands," Journal of Fluorine Chemistry, vol. 121, No. 2, Jun. 1, 2003, pp. 131-134.
Smith, M.B. Organic Synthesis, McGraw-Hill, Inc. 1994, Chapter 1.
Sprenger, et al. "The cyclobutenediylium cation, a novel chromophore from squaric acid," Angew. Chem. International Edition, vol. 6 (1967), No. 6, pp. 553-554.
Suschitzky, H. "Syntheses and Reactions of 2,2'-bisbenzimidazole Systems," J. Heterocyclic Chem. 1999, 36, pp. 1001-1012.
Suzuki, T. et al., "4,7-bis(dimethylamino)benzimidazoles and twin-type derivatives: reversible two-stage redox system modulated by proton-transfer," Tetrahedron Lett. 2003, 44, pp. 7881-7884.
Takahashi et al. "Novel Electron Acceptors for Organic Condcutors: 1,2-Bis(p-benzoquino)-3-[2-(dicyanomethylene)-2,5-thienoquino]cyclopropane Derivatives," J. Chem. Soc., Chem. Commun., 1994, pp. 519-520.
Takahashi et al. "Novel metallic charge-transfer complexes composed of a [3]radialene type acceptor: a 1,2-bis(p-benzoquino)-3-[2-(dicyanomethylene)..." Advanced Materials, July, No. 7, 3 pgs.
Vaid T.P. et al, "Investigations of the 9,10-diphenylacridyl radical as an isostructural dopant for the molecular semiconductor 9,10-diphenylanthracene," Chemistry of Materials, American Chemical Society, Bd. 15, Nr. 22, 4292-4299 (2003).
Vyas, P.C. et al. "A simple synthesis of 2,2'-bis-benzimidazoles," Chem. Industry, 1980, pp. 287-288.
Weiss, M. "Acetic Acid-Ammonium Acetate Reactions. 2-Isoimidazoles as Intermediates in Imidazole Formation," J. Am. Chem. Soc. 1952, 74, pp. 5193-5195.
West, R. et al., "Diquinocyclopropanones, Diquinoethylenes, and the Anion-Radical and Free-Radical Intermediates in their Formation," Dept. of Chemistry, Univ. of Wisconsin, Feb. 24, 1975, pp. 2295-2299.
Wintgens, V. et al., "Reduction of Pyrylium Salts: Study by ESR and UV_Visible Spectroscopy of the Reversible Dimerization of the Pyranyl Radical," New. J. Chem., 10/6, 345-350 (1986).
Yamaguchi, et al., "New Approaches to Tetracyanoquinodimethane," Bull. Chem. Soc. Jpn. 62 (1989) pp. 3036-3037.
Yamamoto, Y. et al. "The Electrical Properties of the Poly(N-vinyl Carbazole)-Antimony (V) Chloride (or Iodine) Charge Transfer Complexes," Bull. Chem. Soc. Jap. 1965, 38, 2015-2017.
Yoshiko, S., et al. "The Quinoid-biradical Tautomerism of 3,6-bis(4,5-diphenyl-2H-imidazol-2-ylidene)-1,4-cyclohexadiene," Nippon Kagaku Kaishi, 1972, 1, pp. 100-103.
Yukihiko, T., et al. "Studies on Aromatic Nitro Compounds. V. A Simple One-Pot Preparation of o-Aminoaroylnitriles from Some Aromatic Nitro Compounds," Chem. Pharm. Bull., 33 (4) 1360-1366 (1985).
Zhou, X et al., "Enhanced hole Injection Into Amorphous Hole-Transport Layers of Organic Light-Emitting Diodes Using Controlled p-Type Doping," Adv. Funct. Mater., 2001, 11, No. 4, pp. 310-314.
Ziegenbein, W. "The cyclobutenediylium cation, a novel chromophore from squaric acid," Angew. Chem., 79:12, pp. 581-582 (1967).
English Translation of Japanese Office Action; Japanese Patent Application No. 2005228491; dated Apr. 17, 2009.
International Search Report, International App. No. PCT/EP2007/002359, dated May 24, 2007.
Final Office Action, U.S. Appl. No. 11/688,777; dated Nov. 27, 2009.
Non-Final Office Action, U.S. Appl. No. 11/688,777; dated Feb. 2, 2009.
Response to Office Action, U.S. Appl. No. 11/688,777; dated Sep. 4, 2009.
Response to Office Action, U.S. Appl. No. 11/688,777; dated Aug. 3, 2009.
Restriction Requirement, U.S. Appl. No. 11/688,777; dated Mar. 5, 2010.
Response to Restriction Requirement, U.S. Appl. No. 11/688,777; dated Apr. 1, 2010.
Notice of Allowance, U.S. Appl. No. 11/196,491; dated Apr. 13, 2009.
Notice of Allowance, U.S. Appl. No. 11/196,491; dated Oct. 20, 2008.
Response to Office Action for U.S. Appl. No. 11/196,491; dated Aug. 11, 2008.
Final Office Action, U.S. Appl. No. 11/196,491; dated Feb. 11, 2008.
Response to Office Action for U.S. Appl. No. 11/196,491; dated Nov. 5, 2008.
Non-Final Office Action, U.S. Appl. No. 11/196,491, dated Jul. 3, 2007.
International Search Report and Preliminary Report on Patentability for PCT/DE2008/001080; dated Jul. 11, 2008.
International Search Report for PCT/DE2008/00654; dated Jun. 15, 2009.
International Search Report and Preliminary Report on Patentability for PCT/EP2006/010816; dated Feb. 9, 2007.
Advisory Action for U.S. Appl. No. 11/315,072 dated Mar. 8, 2010.
Response to Final Office Action for U.S. Appl. No. 11/315,072; dated Feb. 17, 2010.
Final Rejection for U.S. Appl. No. 11/315,072; dated Nov. 16, 2009.
Response to Office Action for U.S. Appl. No. 11/315,072; dated Jul. 29, 2009.
Non-Final Rejection for U.S. Appl. No. 11/315,072; dated Apr. 29, 2009.
Non-Final Rejection for U.S. Appl. No. 11/315,072; dated Nov. 12, 2008.

(56) References Cited

OTHER PUBLICATIONS

Response to Office Action for U.S. Appl. No. 11/315,072; dated Feb. 10, 2009.
European Search Report for EP 07009366; dated Oct. 19, 2007.
International Search Report for PCT/EP2008/003792; dated Sep. 2, 2008.
Disclosure Pursuant to 37 C.F.R. 1.56 for U.S. Appl. No. 12/667,440 (submitted herewith).
Bard, A. J., Faulkner, R.J., Electrochemical Methods: Fundamentals and Applications, Wiley, $2^{nd}$ Ed., 2000 (Chapter 2).
D'Andrade, B.W. et al., "Relationship between the ionization and oxidation potentials of molecular organic semiconductors," Organic Electronics 6, 2005, pp. 11-20.
Gao, W. et al., "Effect of electrical doping on molecular level alignment at organic-organic heterojunctions," Applied Physics Letters, vol. 82, No. 26, Jun. 30, 2003, pp. 4815-4817.
Harada, K. et al. "Organic Homojunction Diodes with a High Built-in Potential: Interpretation of the Current-Voltage Characteristics by a Generalized Einstein Relation," Phys. Rev. Lett. 94, 036601 (2005).
Huang, Jingsong et al., "Low-voltage organic electroluminescent devices using pin structures," Applied Physics Letters, vol. 80, No. 1, Jan. 7, 2002, pp. 139-141.
Kido, Junji et al., "Bright Organic Electroluminescent Devices Having a Metal-doped Electron-injecting Layer," Applied Physics Letters, vol. 73, No. 20, Nov. 16, 1998, pp. 2866-2868.
Maitrot, M. et al., "Molecular material based junctions: Formation of a Schottky Contact with Metallophthalocyanine Thin Films Doped by the Cosublimation Method," J. Applied Physics, 60(7), Oct. 1, 1986, pp. 2396-2400.
Miller, L.L. et al., "A simple comprehensive correlation of organic oxidation and ionization potentials," J. Org. Chem., 1972, vol. 37, No. 6, pp. 916-918.
Pfeiffer, M. et al., "Controlled doping of phthalocyanine layers by cosublimation with acceptor molecules: A systematic Seebeck and conductivity study," Applied Physics Letters, vol. 73, No. 22 Nov. 20, 1998, pp. 3202-3204.
R. Schlaf et al., "Homo/Lumo Alignment at PTCDA/ZnPc and PTCDA/ClInPc Heterointerfaces Determined by Combined UPS and XPS Measurements," J. Phys. Chem. B 1999, 103, pp. 2984-2992.
Tang, C.W. et al., "Organic electroluminescent diodes," Applied Physics Letters, vol. 51, No. 12, Sep. 21, 1987, pp. 913-915.
Tang, T.B. et al., "Ionization thresholds of merocyanine dyes in the solid state," Journal of Applied Physics, vol. 59, (1), Jan. 1986, pp. 5-10.
Werner, A. G. et al., "Pyronin B as a donor for n-type doping of organic thin films," Applied Physics Letters, vol. 82, No. 25, Jun. 23, 2003, pp. 4495-4497.
Yao, Fu et al., "Quantum-chemical predictions of Absolute standard redox potentials of diverse organic molecules and free radicals in acetonitrile," J. Am. Chem. Soc. 2005, 127, pp. 7227-7234.
Zhou, X. et al., "Very low operating voltage organic light-emitting diodes using a p-doped amorphous hole injection layer," Applied Physics Letters, vol. 78, No. 4, Jan. 22, 2001, pp. 410-412.
Zimmerman, T. et al. "Benzocycloalkenone und dihydro-2H, 7H-1-benzopyranone aus 2,4,6-triaryl-pyryliumsalzen und ycloalkane-1,2-dionen," J. Praia. Chem. 331 pp. 306-318 (1989).
Non-Final Rejection for U.S. Appl. No. 12/046,620; dated Nov. 25, 2009.
Response to Restriction Requirement for U.S. Appl. No. 12/046,620; dated Aug. 24, 2009.
Restriction Requirement for U.S. Appl. No. 12/046,620; dated Jul. 22, 2009.
Anderson, J.D. et al., "Electrochemistry and Electrogenerated Chemiluminescence Processes of the Componenets of Aluminum Quinolate/Triarylamine, and Related Organic Light emitting Diodes," J. Am. Chem. Soc., 1998, 120, pp. 9646-9655.
Nollau, A. et al., "Controlled n-type doping of a molecular organic semiconductor: naphthalenetetracarboxylic dianhydride (NTCDA) doped with bis(ethylenedithio)-tetrathiafulvalene (BEDT-TTF)," J. Appl. Phys., vol. 87, No. 9, May 1, 2006, pp. 4340-4343.
Parker, "On the Problem of Assigning Values to Energy Changes of Electrode Reactions," Journal of the American Chemical Society, 96:17, Aug. 21, 1974, pp. 5656-5661.
German Office Action for DE Application No. 10 2007 032 220.4 dated May 12, 2016 (5 pages).
English translation of Examination Notification for Taiwan Application No. 097124804 dated Jan. 28, 2014.
Castaner et al., "Highly crowded perchloropolyphenyl-p-xylylenes with exceptional thermal stability," J. Org. Chem., 1991, 56(18):5445-5448.
Domingo et al., "Inert Carbon Free Radicals. 14. Synthesis, Isolation, and Properties of Two Strongly π-π Interacting Mixed-Valence Compounds: the Perchloro-4,4'-ethynylenebis(triphenylmethyl) Anion Radical Potassium (18-Crown-6) Salt and the Perchloro-α,α,α',α'-tetraphenyl-p-xylylene Anion Radical Tetrabutylammonium Salt," Chem. Mater., 1997, 9(7):1620-1629.
Japanese Office Action for JP Application No. 2010-513645 dated Jun. 25, 2013 (7 pages) (English translation).
English translation of Hirose et al. (JP 04338760 A). Oct. 8, 2012.
German Office Action for DE Application No. 10 2007 031 220.4 dated Jun. 14, 2019 (5 pages).
Eicher et al., "o- and p-(dicyanomethylene)quinocyclopropenes Synthesis, Mechanisms of Formation and Properties," Chem. Ber., 1971, 104:605-638.

QUINOID COMPOUNDS AND THEIR USE IN SEMICONDUCTING MATRIX MATERIALS, ELECTRONIC AND OPTOELECTRONIC STRUCTURAL ELEMENTS

CROSS-REFERENCE TO RELATED APPLICATIONS

This application is a divisional of U.S. patent application Ser. No. 12/667,440, filed Mar. 15, 2010, which is a national phase entry of PCT Patent Application No. PCT/DE2008/001080, filed Jul. 2, 2008, which claims foreign priority to German Patent Application No. 102007031220.4, filed Jul. 4, 2007. Each of these applications is incorporated herein by reference.

The invention relates to quinoid compounds and their use as dopant for the doping of an organic semiconductive matrix material, as charge injection layer, as hole blocker layer, as electrode material, as transport material itself, as storage material in electronic and/or optoelectronic structural elements, as well as to an organic semiconductive material and electronic or optoelectric structural elements.

The changing of organic semiconductors by doping as regards their electrical properties, especially their electrical conductivity, as is also the case for inorganic semiconductors such as silicon semiconductors, is known. Here, an elevation of the conductivity, which is quite low at first, as well as, depending on the type of dopant used, a change in the Fermi level of the semiconductor is achieved by generating charge carriers in the matrix material. A doping results here in an elevation of the conductivity of charge transport layers, which reduces ohmic losses, and in an improved transition of the charge carriers between contacts and organic layer. Inorganic dopants such as alkali metals (e.g., cesium) or Lewis acids (e.g., $FeCl_3$, $SbCl_5$) are usually disadvantageous in organic matrix materials due to their high coefficient of diffusion since the function and stability of the electronic structural elements is adversely affected, see D. Oeter, Ch. Ziegler, W. Göpel Synthetic Metals (1993) 61 147-50; Y. Yamamoto et al. (1965) 2015; J. Kido et al. Jpn J. Appl. Phys. 41 (2002) L358-60. In addition, the latter dopants have such a high vapor pressure that a technical use is very questionable. Moreover, the reduction potentials of these compounds is often too low for doping technically really interesting hole conductor materials. In addition, the extremely aggressive reaction behavior of these dopants makes a technical use difficult.

The basic object of the present invention is to provide compounds that can be used as dopant, as charge injection layer, as hole blocker layer, as electrode material, as transport material itself or as storage material and can overcome the disadvantages of the state of the art. The compounds should preferably have a sufficiently high reduction potential, have no disturbing influences on the matrix material and provide an effective elevation of the charge carrier number in the matrix material and be relatively simple to handle.

Further objects of the present invention consist in indicating possibilities for using these compounds as well as providing organic semiconductive materials and electronic or optoelectronic structural elements in which the disclosed compounds can be used.

For example, dianions and radical anions that are materially the same compounds as the quinoid compounds but are merely present in another oxidation state should be understood as derivatives of the quinoid compounds.

The first object is solved by the quinoid compounds selected from the group consisting of:

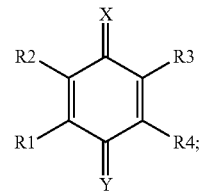

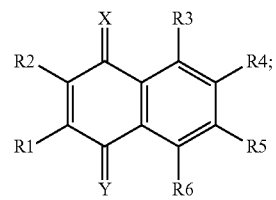

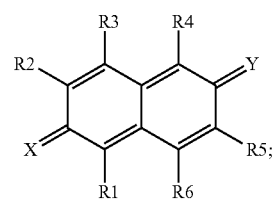

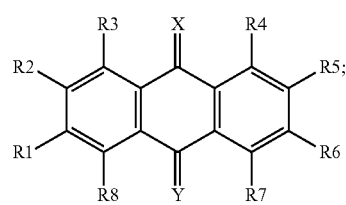

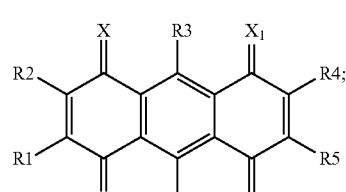

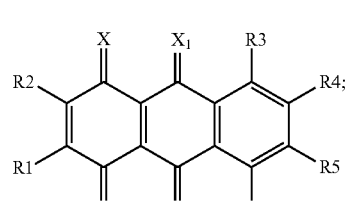

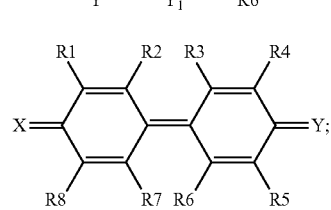

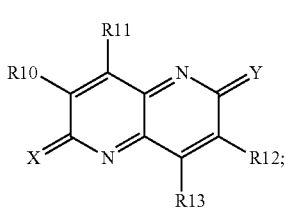

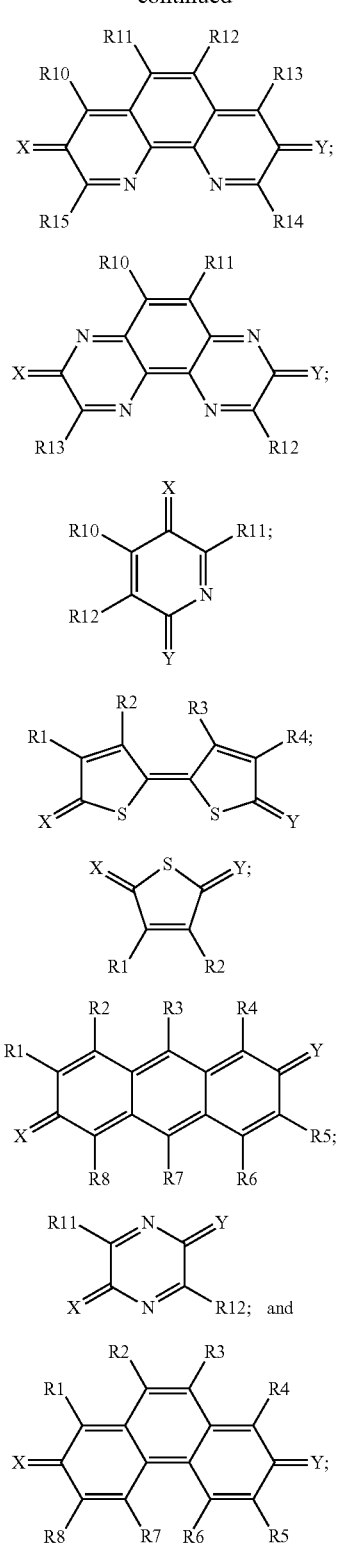

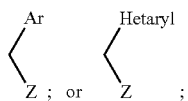

wherein $R^1$-$R^8$ are independently selected from halogen, CN, $NO_2$, COR, perhalogenated or partially halogenated $C_1$-$C_{10}$ alkyl groups, substituted or unsubstituted electron-withdrawing aryl-, or substituted or unsubstituted electron-withdrawing heteroaryl groups; $R^{10}$-$R^{15}$ are independently selected from hydrogen, halogen, CN, $NO_2$, COR, unsubstituted or substituted $C_1$-$C_{10}$ alkyl, $C_1$-$C_{10}$ alkoxy, substituted or unsubstituted electron-withdrawing aryl-, or substituted or unsubstituted electron-withdrawing heteroaryl groups; X, $X_1$, Y, and $Y_1$ are independently selected from:

wherein:
Z is selected from halogen, $NO_2$, NO, $CF_3$, COR, or $SO_2R$; R is selected from substituted or unsubstituted $C_1$-$C_{10}$ alkyl, substituted or unsubstituted aryl, or substituted or unsubstituted heteroaryl; Ar is an acceptor-substituted and halogenated aromatic hydrocarbon; and Hetaryl is an acceptor-substituted and/or halogenated, electron-withdrawing aromatic heterocyclic compound. $R^1$-$R^8$ may be selected independently from fluorine or perfluorinated $C_1$-$C_{10}$ alkyl groups. $R^{10}$-$R^{15}$ may be selected independently from perfluorinated $C_1$-$C_{10}$ alkyl groups. The acceptor substituent of Ar may be a nitrile group, and the other positions of Ar may be halogenated with fluorine atoms. Ar may be a polycyclic compound or biaryl. The acceptor-substituent of Hetaryl may be a nitrile group. Hetaryl may be a polycyclic compound, Hetaryl may be completely halogenated by fluorine. The compounds herein may be included in an electronic or optoelectronic structural element, such as an organic light-emitting diode, a photovoltaic cell, an organic solar cell, an organic diode, or an organic field effect transistor.

It was surprisingly determined that the quinoid compounds in accordance with the invention yield a significantly stronger and/or more stable dopant than previously known acceptor compounds, during which the novel quinoid structures are used in neutral form as p-dopant opposite an organic semi-conductive matrix material.

In particular, the conductivity of charge transport layers is significantly elevated when using the compounds in accordance with the invention and/or the transition of the charge carriers between the contacts and organic layer is significantly improved in applications as electronic structural element. Without being limited by this conception, it is assumed that CT complexes are formed in the use in accordance with the invention of the quinoid structures in a doped layer, especially by the transfer of at least one electron from the particular surrounding material. Also, cations of the matrix material are formed that can move on the matrix material. In this manner the matrix material gains a conductivity that is elevated in comparison to the conductivity of the non-doped matrix material. Conductivities of non-doped matrix materials are as a rule <$10^{-8}$ S/cm, especially frequently <$10^{-10}$ S/cm. Care should be taken here that the matrix materials have a sufficiently high purity. Such purities can be achieved with traditional methods, for example, gradient sublimation. The conductivity of such matrix material can be elevated by doping to greater than $10^{-8}$ S/cm, frequently >$10^{-5}$ S/cm. This is true in particular for matrix materials that have an oxidation potential of greater than −0.5 V vs. Fc/Fc$^+$, preferably greater than 0 V vs. Fc/Fc$^+$, especially greater than +0.2 V vs. Fc/Fc$^+$. The indication Fc/Fc$^+$ refers to a redox pair ferrocene/ferrocenium that is used as reference in an electrochemical determination of potential, for example, cyclovoltammetry.

The quinoid compounds can also be used as hole injection layer. Thus, for example, a layer structure of anode/acceptor/hole transporter can be produced. The hole transporter can be a pure layer or a mixed layer. In particular, the hole transporter can also be doped with an acceptor. The anode can be, for example, ITO. The acceptor layer can be, for example, 0.5-100 nm thick.

It was furthermore established in accordance with the invention that the described quinoid compounds can also be used as injection layer in electronic structural components, preferably between an electrode and a semiconductor layer, that can also be doped, or also as blocker layer, preferably between emitter- and transport layer in electronic structural elements. The compounds used in accordance with the invention have a surprisingly high stability relative to their reactivity with the atmosphere.

Doping

Among others, phthalocyanine complexes, for example, Zn (ZnPc), Cu (CuPc), Ni (NiPc) or other metals can be used as p-dopable matrix material, and the phthalocyanine ligand can also be substituted. Other metal complexes of naphtocyanines and porphyrines can optionally also be used. Furthermore, arylated or heteroarylated amines or benzidine derivatives can also be used as matrix material, which can be substituted or unsubstituted, for example TPD, a-NPD, TDATA, especially also spiro-linked ones such as, e.g., spiro TTB. In particular, a-NPD and spiro TTB can be used as matrix material.

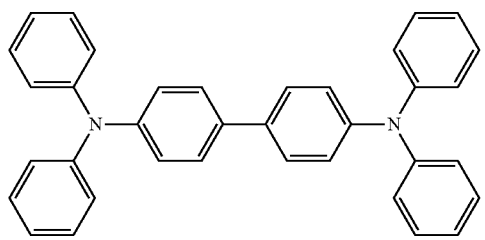

TPD

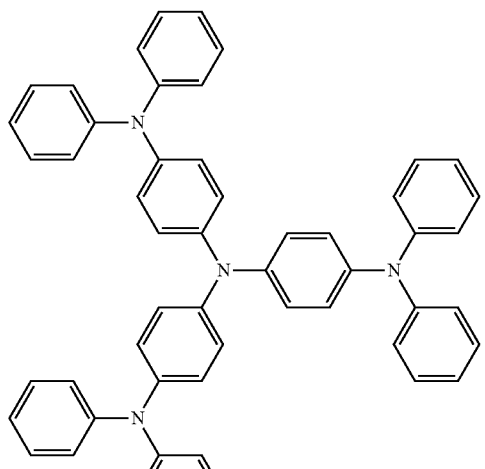

TDATA

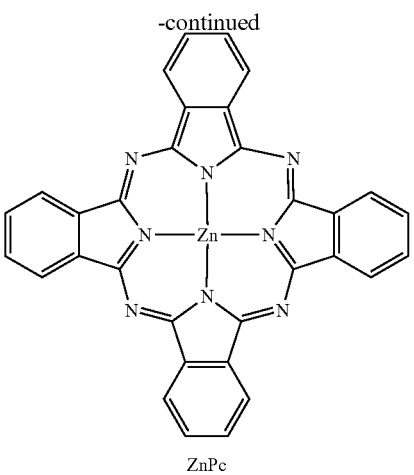

ZnPc

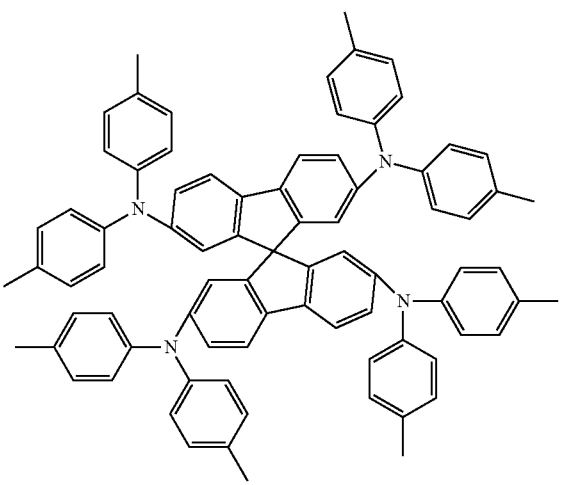

spiro-TTB

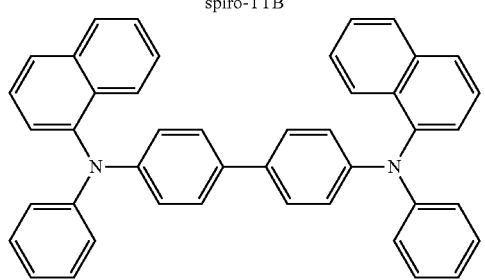

α-NPD

In addition to polyaromatic hydrocarbons heteroaromatics such as in particular imidazole, thiophene, thiazole derivatives, heterotriphenylenes but also others can also be used as matrix material, optionally also dimeric, oligomeric or polymeric heteroaromatics. The heteroaromatics are preferably substituted, especially aryl-substituted, for example phenyl- or naphthyl-substituted. They can also be present as spiro compounds.

It is understood that the named matrix materials can also be used in the frame-work of the invention mixed with each other or with other materials. It is understood that suitable other organic matrix materials can also be used that have semiconductive properties.

Doping Concentration

The dopant is preferably present in a doping concentration of ≤1:1 relative to the matrix molecule or to the monomeric unit of a polymeric matrix molecule, preferably in a doping concentration of 1:2 or less, especially preferably 1:5 or less or 1:10 or less. The doping concentration can be in the range of 1:1 to 1:100,000, especially in the range of 1:5 to 10,000 or 1:10 to 1,000, for example in the range of 1:10 to 1:100 or 1:25 to 1:50 without being limited to the above.

Carrying Out the Doping

The doping of the particular matrix material with the compounds to be used in accordance with the invention can take place by one or a combination of the following processes:

Mixed evaporation in the vacuum with a source for the matrix material and one for the dopant.

Sequential depositing of the matrix material and of the p-dopant on a substrate with subsequent diffusing in of the dopant, especially by thermal treatment.

Doping of a matrix layer by a solution of p-dopant with subsequent evaporation of the solvent, especially by thermal treatment.

Surface doping of a matrix material layer by a layer of dopant applied on the surface.

Production of a solution of matrix molecules and dopant and subsequent production of a layer of this solution by conventional methods such as, for example, evaporation of the solvent or centrifuging.

The doping can optionally also take place in such a manner that the dopant is evaporated out of a precursor compound that releases the dopant during heating and/or irradiation. For example, a carbonyl compound, dinitrogen compound or the like can be used as precursor compound that spits off CO, nitrogen or the like during the release of the dopant and other suitable precursors can also be used such as, for example, salts, e.g., halogenides or the like. The heat necessary for evaporation can be substantially provided by an irradiation and it can also be radiated in a targeted manner into certain bands of the compounds or precursors or compound complexes to be evaporated such as charge transfer complexes in order to facilitate the evaporation of the compounds by dissociation of the complexes, e.g., by transfer into excited states. However, the complex can in particular also be sufficiently stable for evaporating under the given conditions in a non-dissociated manner or for being applied onto the substrate. It is understood that other suitable processes can also be used to carry out the doping.

Thus, p-doped layers of organic semiconductors can be produced in this manner that can be used in multiple ways.

Semi-Conductive Layer

Semiconductive layers can be produced by the quinoid structures used in accordance with the invention that are optionally designed rather linearly such as, e.g., conductivity paths, contacts or the like. The quinoid structures can be used here as p-dopants together with another compound that can function as matrix material and the doping ratio can be 1:1 or less. The dopant used can also be present in higher amounts relative to the particular other compound or component so that the ratio of dopant:compound can be in the ratio of >1:1, for example, in the ratio of ≥2:1, ≥5:1, ≥10:1 or ≥20:1 or higher. The molar doping ratio of dopant to matrix molecule or the doping ratio of dopant to monomeric units of a polymeric matrix molecule may be between 20:1 and 1:100000. The particular other component can be one such as can be used a matrix material in the case of the production of doped layers, without being limited to it. The dopant used can optionally also be present substantially in pure form, for example, as pure layer.

The area containing a dopant or consisting substantially or completely of it can be brought in contact in an electrically current-conducting manner with an organic semiconductive material and/or with an inorganic semiconductive material, for example, arranged on such a substrate.

In particular the quinoid structures are preferably used in accordance with the invention as p-dopants, e.g., in a ratio of ≤1:1 or ≤1:2. For example, when using ZnPc, spiro TTB or a-NPD as matrix semiconductive layers with conductivities at room temperature in the range of $10^{-5}$ S/cm or higher, for example, $10^{-3}$ S/cm or higher, for example, $10^{-2}$ S/cm can be achieved by the electron-withdrawing compounds used in accordance with the invention as p-dopants. When using phthalocyanine zinc as matrix a conductivity of greater than $10^{-8}$ S/cm was achieved, for example $10^{-6}$ S/cm. On the other hand, the conductivity of non-doped phthalocyanine zinc is maximally $10^{-10}$ S/cm.

It is understood that the layer or the structure with the dopants can contain one or more different quinoid structures.

Electronic Structural Element

When using the described compounds to produce p-doped organic semiconductor materials that can be arranged in particular in the form of layers or electronic conduction paths a plurality of electronic structural elements or equipment containing the latter can be produced with a p-doped organic semi-conductor layer. In the sense of the invention the concept "electronic structural elements" also comprises optoelectronic structural elements. The electronic properties of an electronically functionally active area of the structural element such as its electrical conductivity, light-emitting properties or the like can be advantageously changed by using the described compounds. Thus, the conductivity of the doped layers can be improved and/or the improvement of the charge carrier injection of contacts into the doped layer can be achieved.

The invention comprises in particular organic light-emitting diodes (OLED), organic solar cells, field effect transistors, organic diodes, in particular those with a high rectification ratio such as $10^3$-$10^7$, preferably $10^4$-$10^7$ or $10^5$-$10^7$, and organic field effect transistors that were produced by the electron-withdrawing quinoid structures. An electron-withdrawing group or acceptor group or electron-withdrawing structures should be understood in such a manner according to the present invention that they have a stronger electron-withdrawing effect than hydrogen. The concept "electron-withdrawing aryl- and heteroaryl groups" denotes aromatics and/or heteroaromatics that are electron-poor according to the invention and have a lower electron density than benzene.

In the electronic structural element a p-doped layer based on an organic matrix material can be present, for example, in the following layer structures, in which the base materials or matrix materials of the individual layers are preferably organic:

p-i-n: p-doped semiconductor-intrinsic semiconductor-n-doped semiconductor, n-i-p: n-doped semiconductor-intrinsic semiconductor-p-doped semiconductor.

"i" is again a non-doped layer, "p" is a p-doped layer. The contact materials are hole-injecting here and on the p side, for example, a layer or a contact of ITO or Au can be provided, or electron-injecting, and on the n side a layer or a contact of ITO, Al or Ag can be provided.

In the above structures the i layer can also be omitted if necessary, in which case layer sequences with p-n or n-p transitions can be obtained.

However, the use of the described compounds is not limited to the above-cited exemplary embodiments, in particular, the layer structures can be supplemented or modified by the introduction of additional suitable layers. In particular, OLEDs with such layer sequences, in particular with pin structure or with a structure inverse to it, can be built up with the described compounds.

In particular, organic diodes of the metal-insulator-p-doped semiconductor type (min) or also optionally of the pin type can be produced with the aid of the described p-dopants, for example on the basis of phthalocyanine zinc. These diodes display a rectification ratio (rectification ratio, relative to the current flow in the direction of passage in contrast to the current flow in the reverse direction of the structural part) of $10^5$ and higher. Furthermore, electronic structural elements with p-n transitions can be produced using the cited compounds, in which the same semiconductor material is used for the p- and the n-doped side (homo p-n transition).

However, the compounds in accordance with the invention can also be used in the electronic structural elements in layers, conductivity paths, point contacts or the like if they predominate relative to another component, for example, as injection layer in pure or substantially pure form.

Further objects and advantages of the present invention will now be described in an illustrative manner using the following examples that are to be considered solely as illustrative and not as limiting the scope of the invention.

Preparation of the Quinoid Compounds

The quinoid compounds in accordance with the invention can be synthesized from the appropriate dihydro compounds by oxidation according to known processes, which dihydro compounds can be prepared from electron-poor aromatics or heteroaromatics by nucleophilic substitution of CH-acidic compounds, see L. Brucsis, K. Friedrich Chem. Ber. 109 (1976) 2469-74; S. Yamaguchi et al. Bull. Chem. Soc. Jpn. 62 (1989) 3036-7; E. L. Martin U.S. Pat. No. 3,558,671, as is shown here using the example of the hexafluorobenzene a and a cyanotetrafluorobenzene acetonitrile compound b in the following equation.

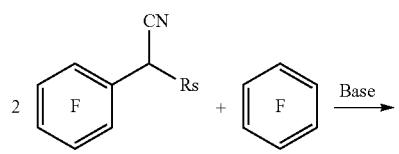

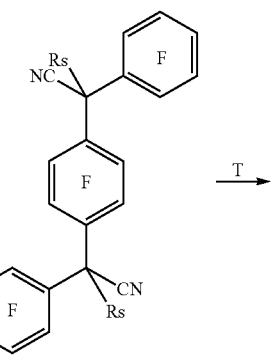

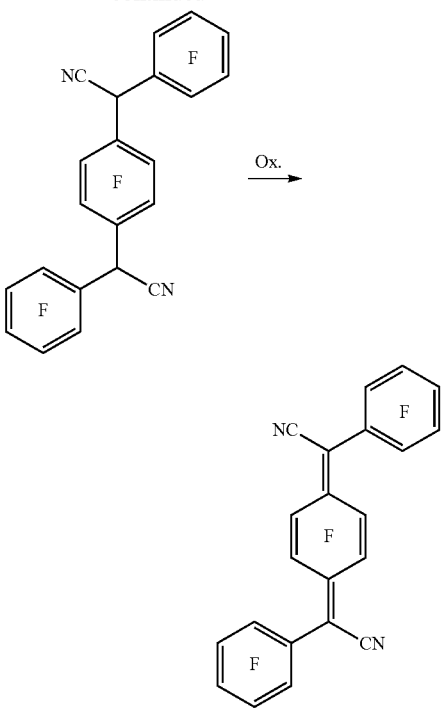

Rs = Alkyl, Si(Alkyl)3, SAlkyl, H

A protective group on the CH-acidic reactants such as, e.g., alkyl, benzyl, trialkylsilyl or thioalkoxy can be advantageous for the second substitution.

EXAMPLES OF SYNTHESIS

Dihydro Compounds

Synthesis of 4,4'-Decafluorodibenzhydryenl-2,3,5,6,2',3',5',6'-octafluorobiphenylene

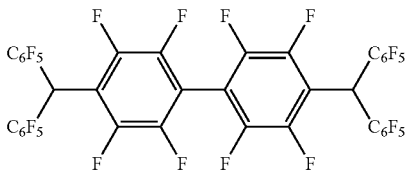

2 eq dipentafluorophenyl-t-butylmethane in a little glyme are slowly compounded under ice cooling and protective gas to a suspension of 2 eq sodium hydride in glyme. After the addition has been concluded the mixture is agitated 30 min longer at room temperature. 1 eq decafluorobiphenyl is rapidly added and the mixture heated 3 h at 60° C. After cooling off, the mixture is precipitated with water and washed with a little methanol and ether. The obtained product is converted in an atmosphere of protective gas for a few minutes in boiling diphenylether under splitting off of butane into the yellow-orangish product, which can be removed by suction after cooling off. Fp.: >250° C.

Synthesis of 3,6 bis[1-cyano-1-(4-cyano-tetrafluoro-phenyl)-methylene]-2,5-difluoro-phenyl-1,4-dicarbonitrile

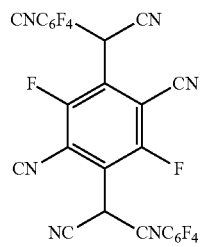

2.5 mmol tetrafluoroterephthalonitrile and 5.1 mmol NaH were suspended in 50 ml dimethoxyethylene under argon. 6.0 mmol (1.28 g) 2-t-butyl-4'-cyanotetrafluorophenylacetonitrile in 5 ml dimethoxyethylene were dropped at 5° C. into this mixture. After 30 h agitation at room temperature the mixture was poured onto 200 ml ice water and acidified with hydrochloric acid. The purple-colored solid obtained was filtered off and dried in the vacuum. The product was purified by recrystallization from a suitable solvent and butane subsequently split off in diphenylether at 250° C. After cooling off, ether was added and the mixture adjusted cold. The precipitated product was removed by suction and dried in the vacuum. (yield 1.55 g). ESE-MS analysis (negative detection, direct inlet from a solution in MeOH/0.5 mM NH4OAc): m/z=587 [M-H]$^-$, 293 [M-2H]$^{2-}$.

Synthesis of the Quinoid Compounds (Oxidation)

Synthesis von 3,6-bis[1-cyano-1-(4-cyano-phenyl)-methylidene]-2,5-difluoro-cyclohexa-1,4-diene-1,4-dicarbonitrile

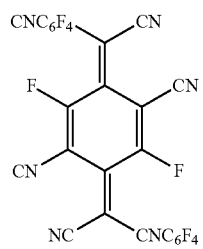

The corresponding dihydro compound was compounded without further purification to the complete solution with glacial acetic acid and a mixture of nitric acid and hydrobromic acid cooled to 0° C. added. After the conclusion of the addition the mixture was agitated still at room temperature, compounded with water until the start of the precipitation of a solid and agitated further at room temperature. The orange-colored solid was removed by suction, washed with water and dried in the vacuum (yield over all stages 76%). DI-MS (EI): m/z=586 [M]$^+$. $^{19}$F-NMR (CD$_3$CN): δ=−100.5 (m, 2F), −127.7 (m, 4F), −131.6 (m, 4F) ppm.

APPLICATION EXAMPLES FOR THE DOPING

An extremely electron-poor and electron-withdrawing quinoid compound is provided very cleanly.

The electron-poor quinoid compound placed in a receiver is evaporated simultaneously with the matrix material. According to the exemplary embodiment the matrix material is phthalocyanine zinc, spiro-TTB or a-NDP. The p-dopant and the matrix material can be evaporated in such a manner that the layer precipitated on a substrate in a vacuum evaporation system has a doping ratio of p-dopant to matrix material of 1:10.

The particular layer of the organic semi-conductor material doped with the p-dopant is applied on an ITO layer (indium tin oxide) arranged on a glass substrate. After the application of the p-doped organic semiconductor layer a metal cathode is applied, for example, by vapor-depositing a suitable metal in order to produce an organic light-emitting diode. It is understood that the organic light-emitting diode can also have a so-called inverted layer construction in which the layer sequence is: glass substrate-metal cathode-p-doped organic layer-transparent conductive cover layer (for example ITO). It is understood that further layers can be provided between the individual cited layers depending on the application.

Doping with_3,6-bis[1-cyano-1-(4-cyano-phenyl)-methylidene]-2,5-difluoro-cyclohexa-1,4-diene-1,4-dicarbonitrile The doping performance was checked by Co evaporation of 3,6-bis[1-cyano-1-(4-cyano-phenyl)-methylidene]-2,5-difluoro-cyclohexa-1,4-diene-1,4-dinitrile (5 mol %) with spiro TTB and measuring the conductivity of the mixed layer obtained. A conductivity of the doped layer of 1.8× 10$^{-4}$ Scm$^{-1}$ was found.

The features of the invention disclosed in the above description and in the claims can be essential individually as well as in any combination for the realization of the invention in its different embodiments.

The invention claimed is:
1. A quinoid compound or derivative thereof, wherein the quinoid compound is selected from the group consisting of:

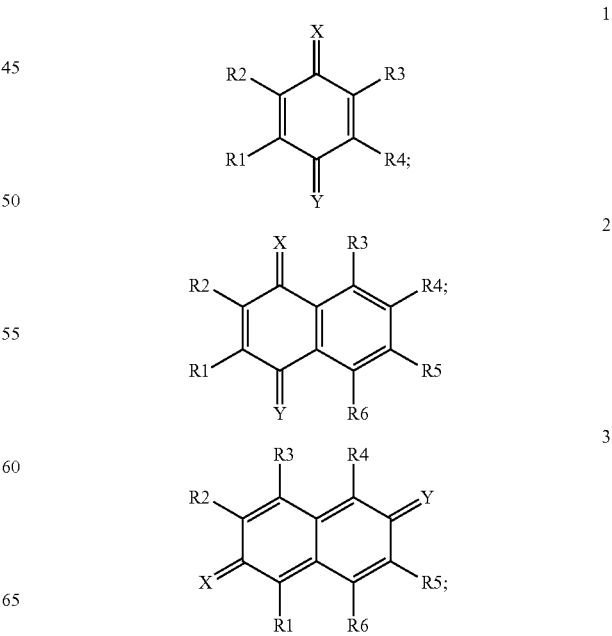

-continued

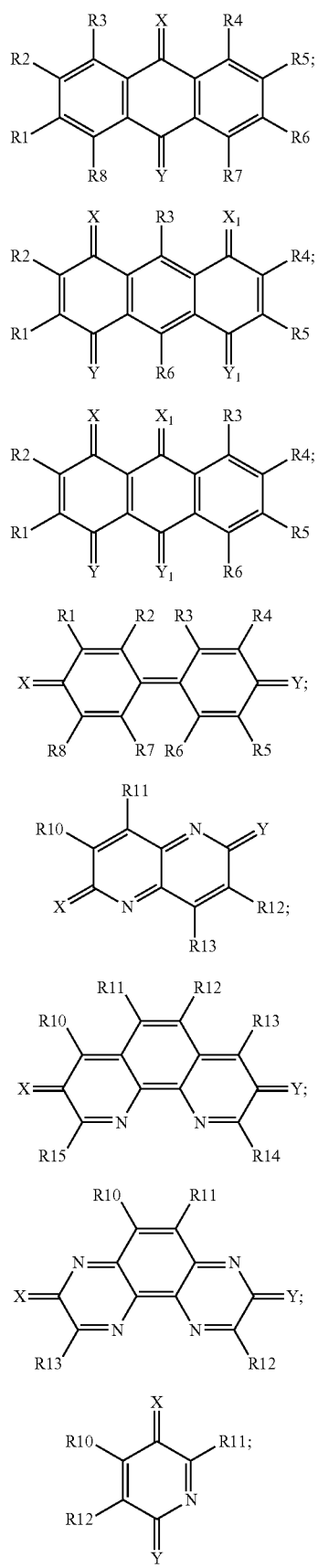

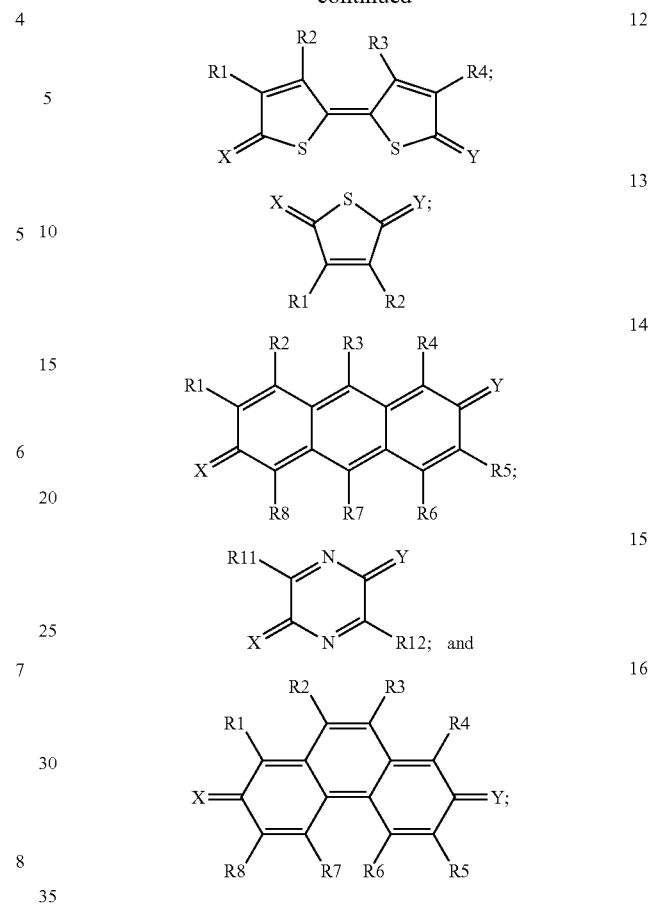

wherein:
R¹-R⁸ are independently selected from halogen, CN, NO₂, COR, perhalogenated or partially halogenated $C_1$-$C_{10}$ alkyl groups, substituted or unsubstituted electron-withdrawing aryl-, or substituted or unsubstituted electron-withdrawing heteroaryl groups;

R¹⁰-R¹⁵ are independently selected from hydrogen, halogen, CN, NO₂, COR, $C_1$-$C_{10}$ alkyl, perfluorinated $C_1$-$C_{10}$ alkyl, $C_1$-$C_{10}$ alkoxy, substituted or unsubstituted electron-withdrawing aryl-, or substituted or unsubstituted electron-withdrawing heteroaryl groups;

X, X₁, Y, and Y₁ are independently selected from:

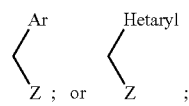

wherein:
Z is selected from halogen, NO₂, NO, CF₃, COR, or SO₂R;
R is selected from substituted or unsubstituted $C_1$-$C_{10}$ alkyl, substituted or unsubstituted aryl, or substituted or unsubstituted heteroaryl;
Ar is an acceptor-substituted and halogenated aromatic hydrocarbon; and
Hetaryl is an acceptor-substituted and/or halogenated, electron-withdrawing aromatic heterocyclic compound.

2. The quinoid compounds according to claim 1, wherein $R^1$-$R^8$ are selected independently from fluorine or perfluorinated $C_1$-$C_{10}$ alkyl groups.

3. The quinoid compounds according to claim 1, wherein $R^{10}$-$R^{15}$ are selected independently from perfluorinated $C_1$-$C_{10}$ alkyl groups.

4. The quinoid compounds according to claim 1, wherein the acceptor substituent of Ar is a nitrile group, and the other positions of Ar are halogenated with fluorine atoms.

5. The quinoid compounds according to claim 1, wherein Ar is a polycyclic compound or biaryl.

6. The quinoid compounds according to claim 1, wherein the acceptor-substituent of Hetaryl is a nitrile group.

7. The quinoid compounds according to claim 1, wherein Hetaryl is a polycyclic compound.

8. The quinoid compounds according to claim 1, wherein Hetaryl is completely halogenated by fluorine.

9. An electronic or optoelectronic structural element comprising a dopant for doping an organic semiconductive matrix material, a charge injection layer, a hole blocker layer, an electrode material, a transport material, or a storage material, wherein the dopant for doping an organic semiconductive matrix material, the charge injection layer, the hole blocker layer, the electrode material, the transport material, or the storage material comprises a quinoid compound or derivative thereof, wherein the quinoid compound is selected from the group consisting of:

1
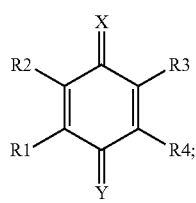

2
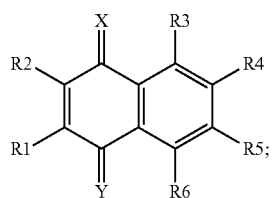

3
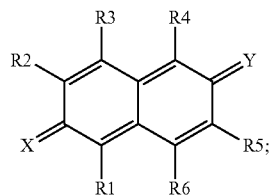

4
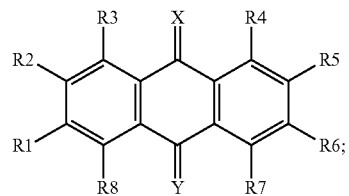

-continued

5
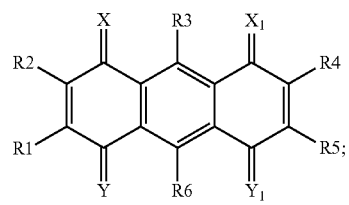

6
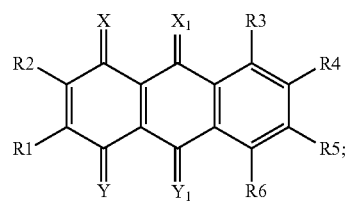

7
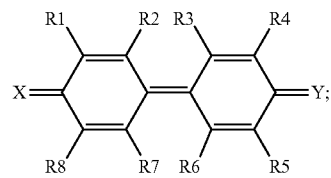

8
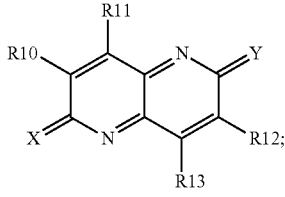

9
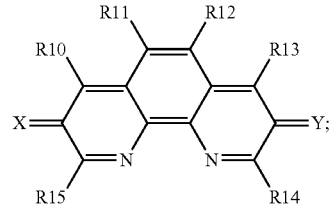

10
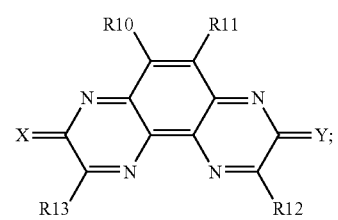

11
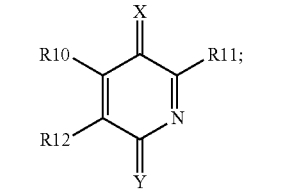

12
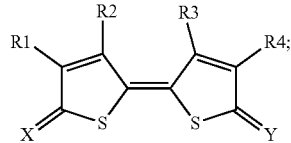

-continued

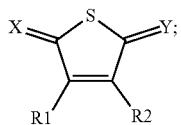

13

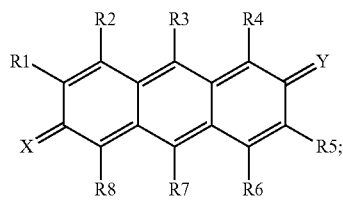

14

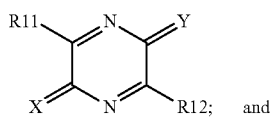

and

15

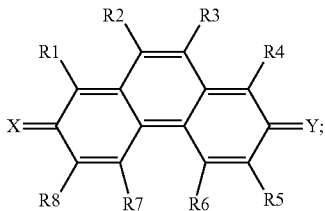

16 wherein:

R¹-R⁸ are independently selected from halogen, CN, NO₂, COR, perhalogenated or partially halogenated $C_1$-$C_{10}$ alkyl groups, substituted or unsubstituted electron-withdrawing aryl-, or substituted or unsubstituted electron-withdrawing heteroaryl groups;

R¹⁰-R¹⁵ are independently selected from hydrogen, halogen, CN, NO₂, COR, $C_1$-$C_{10}$ alkyl, perfluorinated $C_1$-$C_{10}$ alkyl, $C_1$-$C_{10}$ alkoxy, substituted or unsubstituted electron-withdrawing aryl-, or substituted or unsubstituted electron-withdrawing heteroaryl groups;

X, X₁, Y, and Y₁ are independently selected from:

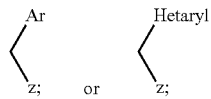

wherein:

Z is selected from halogen, NO₂, NO, CF₃, COR, or SO₂R;

R is selected from substituted or unsubstituted $C_1$-$C_{10}$ alkyl, substituted or unsubstituted aryl, or substituted or unsubstituted heteroaryl;

Ar is an acceptor-substituted and halogenated aromatic hydrocarbon; and

Hetaryl is an acceptor-substituted and/or halogenated, electron-withdrawing aromatic heterocyclic compound.

10. The electronic or optoelectronic structural element of claim 9, comprising the organic semiconductive matrix material and the dopant, wherein the dopant comprises at least one of the quinoid compounds or derivatives thereof.

11. The electronic or optoelectronic structural element according to claim 10, wherein the molar doping ratio of dopant to matrix molecule or the doping ratio of dopant to monomeric units of a polymeric matrix molecule is between 20:1 and 1:100000.

12. The electronic or optoelectronic structural element according to claim 9, comprising an electronically functionally active area, wherein the electronically active area comprises at least one of the quinoid compounds or derivatives thereof.

13. The electronic or optoelectronic structural element according to claim 12, wherein the electronically active area comprises the organic semiconductive matrix material doped with at least one of the dopant, wherein the dopant changes the electronic properties of the organic semiconductive matrix material, wherein the dopant comprises at least one of the quinoid compounds or derivatives thereof.

14. The electronic or optoelectronic structural element according to claim 12, wherein the element is an organic light-emitting diode, a photovoltaic cell, an organic solar cell, an organic diode, or an organic field effect transistor.

* * * * *